United States Patent [19]

VandenBerg

[11] Patent Number: Plant 7,587

[45] Date of Patent: Jul. 9, 1991

[54] CHRYSANTHEMUM PLANT NAMED JESSICA

[75] Inventor: Cornelius P. VandenBerg, Salinas, Calif.

[73] Assignee: Yoder Brothers, Inc., Barberton, Ohio

[21] Appl. No.: 458,839

[22] Filed: Dec. 29, 1989

[51] Int. Cl.[5] ..... A01H 5/00

[52] U.S. Cl. ..... Plt./78

[58] Field of Search ..... Plt./78

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Jessica particularly characterized by its flat capitulum form; decorative capitulum type; yellow ray floret color; diameter across face of capitulum of from 50 to 63 mm when fully opened; spreading and prolific branching pattern; average natural season flowering data of August 22 in Salinas, Calif., and September 21 in Hightstown, N.J.; uniform seven week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandilfora,* and referred to by the cultivar name Jessica.

Jessica, identified as 85-061002, was originated from a cross made by the inventor Cornelius P. VandenBerg in a controlled breeding program in Salinas, Calif., in 1985.

The female parent of Jessica was the cultivar identified as Goldmine, a round, dark yellow formal decorative disclosed in U.S. Plant Pat. No. 5,661. The male parent of Jessica was an unnamed seedling identified as 82-N13009, a yellow daisy.

Jessica was discovered and selected as one flowering plant within the progeny of the stated cross by Cornelis P. VandenBerg in January 1986, in a controlled environment in Salinas, Calif.

The first act of asexual reproduction of Jessica was accomplished when vegetative cuttings were taken from the initial selection in April 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Jessica are firmly fixed and are retained through successive generations of asexual reproduction.

Jessica has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Jessica, which, in combination, distinguish this Chrysanthemum as a new and distinct cultivar:

1. Flat capitulum form.
2. Decorative capitulum type.

3. Yellow ray floret color.
4. Diameter across face of capitulum of from 50–63 mm when fully opened.
5. Medium plant height averaging 30.5 cm from soil line at time of flowering, based on a planting date of June 15 under natural daylength in Hightstown, N.J.
6. Spreading and prolific branching pattern, with an average of eight (8) branches per plant after pinch two weeks after planting a rooted cutting in Hightstown, N.J.
7. Average natural season flowering date of August 22 in Salinas, Calif., and September 21 in Hightstown, N.J., based on several years of trial flowering.
8. Uniform seven week photoperiodic flowering response to short days in photoperiodic controlled flowering programs.
9. Durable, uniform performance.

The accompanying photographic drawings show typical inflorescence and leaf characteristics of Jessica, with the colors being as nearly true as possible with illustrations of this type.

Sheet 1 is a color photograph of Jessica grown as pinched spray pot mum in a 15 cm pot.

Sheet 2 is a black and white photograph of three views of the inflorescence of Jessica.

Sheet 3 is a black and white photograph showing the upper and under sides of the leaves of Jessica at three stages of development (mature, intermediate and immature).

Of the commercial garden mum cultivars known to the inventor, the most similar in comparison to Jessica is the cultivar identified as Fortune, a golden yellow decorative, disclosed in U.S. Plant Pat. No. 5,242. Reference is made to attached Chart A which compares certain characteristics of Jessica to the same characteristics of Fortune.

Similar traits are capitulum form and type, and controlled response period. Jessica is bright yellow, while Fortune is a light golden yellow. Jessica also has a more prolific branching pattern, a smaller diameter of capitulm, and a much earlier natural season flowering date than Fortune.

In the following description color references are made to The Royal Horticultural Society Colour Chart. The color values were determined on plant material grown in a controlled greenhouse environment in Salinas, Calif., on Sept. 15, 1989.

Classification:

*Botanical.*—*Dendranthema grandiflora* cv Jessica.

*Commercial.*—Flat decorative spray pot mum and garden mum.

INFLORESCENCE

A. Capitulum:

*Form.*—Flat.

*Type.*—Decorative.

*Diameter across face.*—50–63 mm when fully opened.

B. Corolla of Ray Florets:

*Color (general tonality from a distance of three meters).*—Yellow.

*Color (upper surface).*—Inner petals 9A; outer petals 6A.

*Color (under surface)*—6B to 6 C.

*Shape.*—Flat, straight, oblong.

C. Corolla of Disc Florets:

*Color (mature).*—14A to 14B.

*Color (immature)*—Closest to 154A to 154B.

D. Reproductive Organs:

*Androecium.*—Present on disc florets only; very few; very scant pollen.

*Gynoecium.*—Present on both ray and disc florets.

PLANT

A. General Appearance:

*Height.*—Medium.

*Branching pattern.*—Spreading and prolific.

B. Foliage

*Color (upper surface).*—147A.

*Color (under surface).*—147B.

*Shape.*—See photograph.

CHART A

COMPARISON OF JESSICA AND FORTUNE

| CHARACTERISTIC | JESSICA | FORTUNE |
|---|---|---|
| Ray Floret Color | Yellow | Light golden-yellow |
| Capitulum Form and Type | Flat decorative | Flat decorative |
| Branching Pattern | Spreading and prolific | Spreading |
| Diameter Across Face of of Capitulum | 50–63 mm | 63 to 70 mm |
| Controlled Response | 7 weeks | 7 weeks |
| Average Natural Season Flower date: | | |
| In Salinas, California: | August 22 | September 3 |
| In Hightstown, New Jersey: | September 21 | October 1 |

Comparisons Made of Plants Grown Under Natural Season Outdoor Conditions In Salinas, California and in Hightstown, New Jersey

I claim:

1. A new and distinct Chrysanthemum plant named Jessica, as described and illustrated.

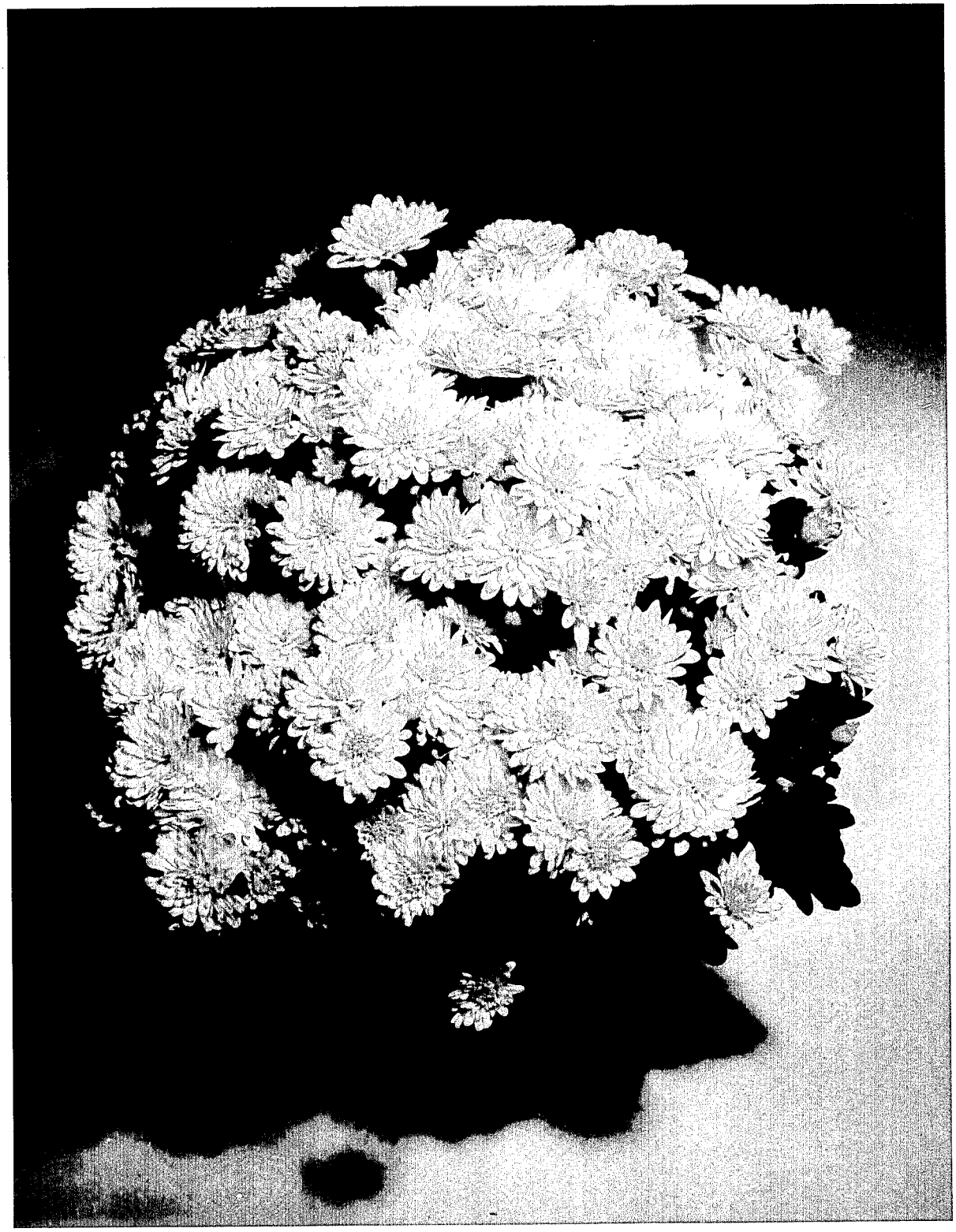

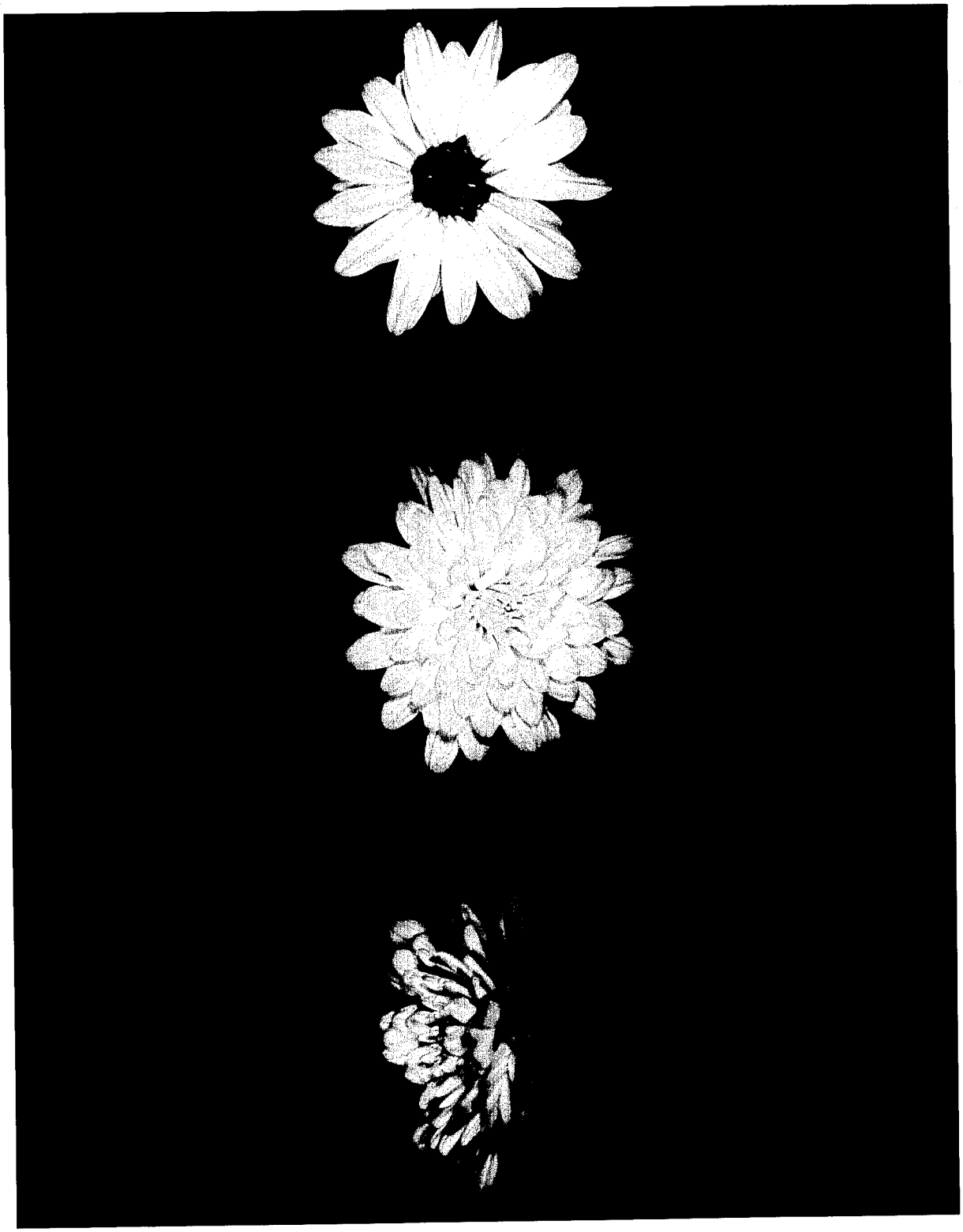

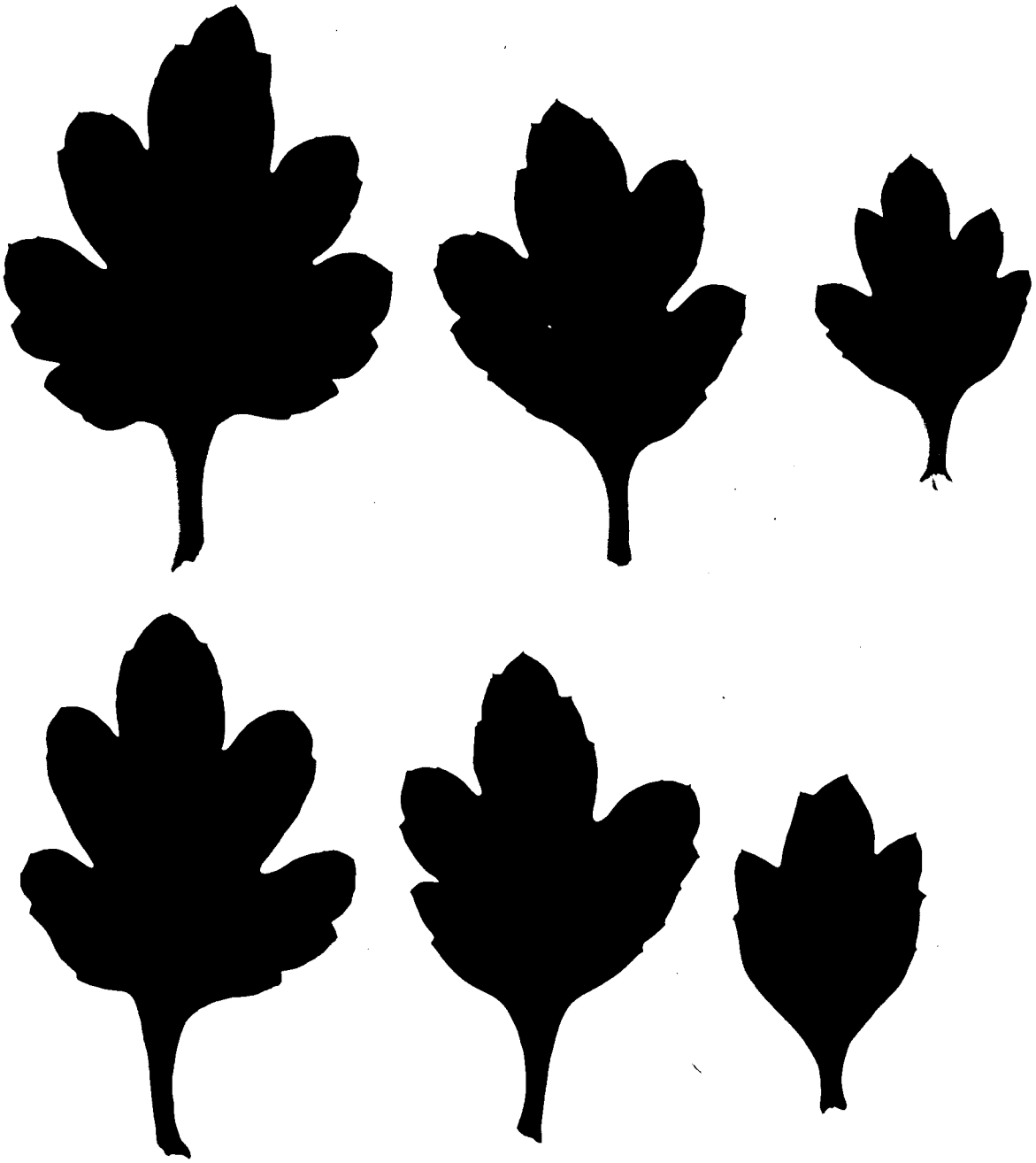

* * * * *